United States Patent
Kitazoe et al.

(10) Patent No.: US 12,226,214 B2
(45) Date of Patent: Feb. 18, 2025

(54) BIOMEDICAL ELECTRODE, BIOMEDICAL SENSOR, AND BIOMEDICAL SIGNAL MEASUREMENT SYSTEM

(71) Applicant: SUMITOMO BAKELITE CO., LTD., Tokyo (JP)

(72) Inventors: Katsuma Kitazoe, Tokyo (JP); Takuya Harada, Tokyo (JP); Takashi Yagisawa, Tokyo (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 624 days.

(21) Appl. No.: 17/620,771

(22) PCT Filed: May 8, 2020

(86) PCT No.: PCT/JP2020/018639
§ 371 (c)(1),
(2) Date: Dec. 20, 2021

(87) PCT Pub. No.: WO2020/261773
PCT Pub. Date: Dec. 30, 2020

(65) Prior Publication Data
US 2023/0020433 A1 Jan. 19, 2023

(30) Foreign Application Priority Data

Jun. 25, 2019 (JP) .................. 2019-117492

(51) Int. Cl.
*A61B 5/268* (2021.01)
*A61B 5/263* (2021.01)
*A61B 5/291* (2021.01)

(52) U.S. Cl.
CPC ............. *A61B 5/263* (2021.01); *A61B 5/268* (2021.01); *A61B 5/291* (2021.01); *A61B 2562/225* (2013.01)

(58) Field of Classification Search
CPC .......... A61B 5/263; A61B 5/268; A61B 5/291
See application file for complete search history.

(56) References Cited

U.S. PATENT DOCUMENTS

2013/0331821 A1* 12/2013 Okada ................ C09C 1/3081
604/525
2015/0274929 A1* 10/2015 Brick ................... C08L 83/00
428/36.9

(Continued)

FOREIGN PATENT DOCUMENTS

JP 2016-163688 9/2016

OTHER PUBLICATIONS

International Search Report and Written Opinion for International Application No. PCT/JP2020/018639 mailed on Aug. 4, 2020, 8 pages.

*Primary Examiner* — Daniel L Cerioni
(74) *Attorney, Agent, or Firm* — Amin, Turocy & Watson, LLP

(57) ABSTRACT

A biomedical electrode according to the present invention includes: a plate-shaped support portion; an elastic pillar portion that is provided on a first surface of the plate-shaped support portion; and a conductive resin layer that is formed to cover a distal end of the elastic pillar portion, in which when measured at 37° C. according to JIS K 6253 (1997), a type A durometer hardness of a surface of the elastic pillar portion is higher than 35 and 65 or lower.

13 Claims, 4 Drawing Sheets

(56) References Cited

U.S. PATENT DOCUMENTS

2016/0089045 A1   3/2016  Sadeghian-Motahar et al.
2016/0230008 A1*  8/2016  Murai ...................... C08L 7/00
2018/0235500 A1   8/2018  Lee et al.

* cited by examiner

BIOMEDICAL ELECTRODE, BIOMEDICAL SENSOR, AND BIOMEDICAL SIGNAL MEASUREMENT SYSTEM

TECHNICAL FIELD

The present invention relates to a biomedical electrode, biomedical sensor, and a biomedical signal measurement system.

BACKGROUND ART

Various biomedical electrodes have been developed until now. As such a technique, for example, a technique described in Patent Document 1 is known. Patent Document 1 describes an electroencephalographic electrode including: a base material that is formed of an elastic body; and a structure that is formed on a surface of the base material (claim 1 and FIG. 1 in Patent Document 1). Patent Document 1 describes that the Shore A hardness of the base material is 68 to 75 A (paragraph 0016 of Patent Document 1).

RELATED DOCUMENT

Patent Document

[Patent Document 1] Japanese Laid-open patent publication NO. 2016-163688

SUMMARY OF THE INVENTION

However, as a result of a thorough investigation, the present inventors found that there is a room for improvement of the electroencephalographic electrode described in Patent Document 1 from the viewpoint of improving low contact resistance, measurement stability, and wearing stability.

The present inventors further conducted an investigation and found that, in a biomedical electrode including an elastic pillar portion, followability to a measurement target or a variation in the measured value of a bioelectrical potential can be appropriately controlled by using the rubber hardness of a portion in contact with a living body such as a scalp or a skin as a guideline. As a result of thorough investigation based on this finding, the present inventors found that by adjusting the rubber hardness of the biomedical electrode to be in a predetermined numerical range, the low contact resistance, the measurement stability, and the wearing stability can be improved, thereby completing the present invention.

According to the present invention, there is provided a biomedical electrode including:
  a plate-shaped support portion;
  an elastic pillar portion that is provided on a first surface of the plate-shaped support portion; and
  a conductive resin layer that is formed to cover distal ends of the elastic pillar portions,
  in which when measured at 37° C. according to JIS K 6253 (1997), a type A durometer hardness of a surface of the elastic pillar portion is higher than 35 and 65 or lower.

In addition, according to the present invention, there is provided a biomedical sensor including the above-described biomedical electrode.

In addition, according to the present invention, there is provided a biomedical signal measurement system including the above-described biomedical sensor.

The present invention provides a biomedical electrode having excellent low contact resistance, measurement stability and wearing stability, and a biomedical sensor and a biomedical signal measurement system including the biomedical electrode.

BRIEF DESCRIPTION OF THE DRAWINGS

FIGS. 1A and 1B are schematic diagrams showing the summary of an example of a biomedical electrode according to an embodiment, in which FIG. 1A is a perspective view and FIG. 1B is a cross-sectional view taken along line A-A of FIG. 1A.

FIGS. 3A and 3B are schematic diagrams showing the summary of another example of the biomedical electrode according to the embodiment, in which FIG. 3A is a perspective view and FIG. 3B is a cross-sectional view taken along line A-A of FIG. 3A.

FIGS. 4A and 4B are schematic diagrams showing the summary of another example of the biomedical electrode according to the embodiment, in which FIG. 4A is a perspective view and FIG. 4B is a cross-sectional view taken along line A-A of FIG. 4A.

DESCRIPTION OF EMBODIMENTS

Figure 1A:
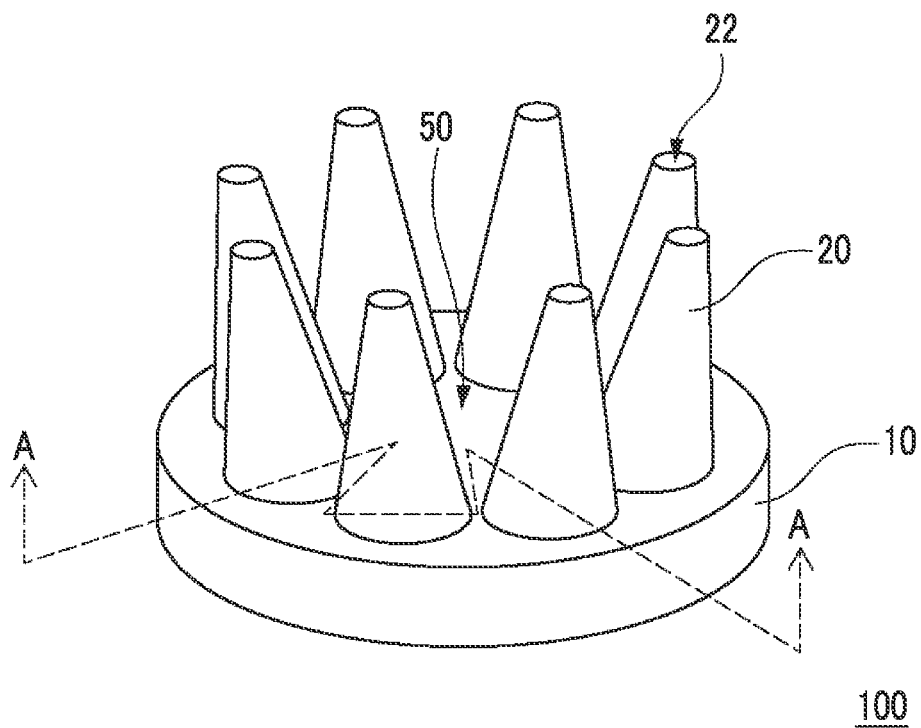

An embodiment of the present invention will be described using the drawings.

An embodiment will be described by defining front, rear, right, left, upper, and lower directions as shown in the drawings. However, the directions are defined for convenience of easy understanding of a relationship between components. Accordingly, this definition does not limit directions during the manufacturing or use of a product according to the present invention.

In all the drawings, the same components will be represented by the same reference numerals, and the description thereof will not be repeated. In addition, the drawings are schematic diagrams, in which a dimensional ratio does not match the actual one.

In this specification, the term "substantially" includes a range in consideration of a tolerance, a variation, or the like during manufacturing unless explicitly specified otherwise.

A biomedical electrode according to the embodiment includes: a plate-shaped support portion; an elastic pillar portion that is provided on a first surface of the plate-shaped support portion; and a conductive resin layer that is formed to cover a distal end of the elastic pillar portion. The biomedical electrode has a configuration in which, when measured at 37° C. according to JIS K 6253 (1997), a type A durometer hardness (also referred to as "rubber hardness") of a surface of the elastic pillar portion is higher than 35 and 65 or lower.

According to the finding of the present inventors, it was found that, in a biomedical electrode including an elastic pillar portion, followability to a measurement target or a variation in the measured value of a bioelectrical potential can be appropriately controlled by using the rubber hardness of a portion in contact with a living body such as a scalp or a skin as a guideline. In addition, it was found that, by adjusting the rubber hardness to be in a predetermined numerical range, low contact resistance, measurement stability, and wearing stability can be improved.

A detailed mechanism is not clear but is presumed to be that: when an elastic pillar portion is excessively flexible, deformation of the elastic pillar portion becomes severe such that the contact resistance increases; and when the elastic pillar portion is excessively hard, the elastic pillar portion does not follow a surface of a living body such that the contact resistance increases. In addition, it is presumed that, due to its appropriate hardness, the elastic pillar portion is likely to push aside the hair of the scalp such that the brain wave acquisition ratio increases.

The biomedical electrode according to the embodiment can detect a variation in bioelectrical potential such as brain wave, heartbeat, muscular activity, or nervous system activity. The biomedical electrode can further include a connector or an electronic component to configure a biomedical sensor that can be connected to an external apparatus. This biomedical sensor is wearable. By analyzing the bioelectrical potential such as a brain wave detected from the biomedical sensor, a biomedical signal measurement system corresponding to various uses can be constructed.

Hereinafter, the biomedical electrode according to the embodiment will be described below.

Figure 1B:
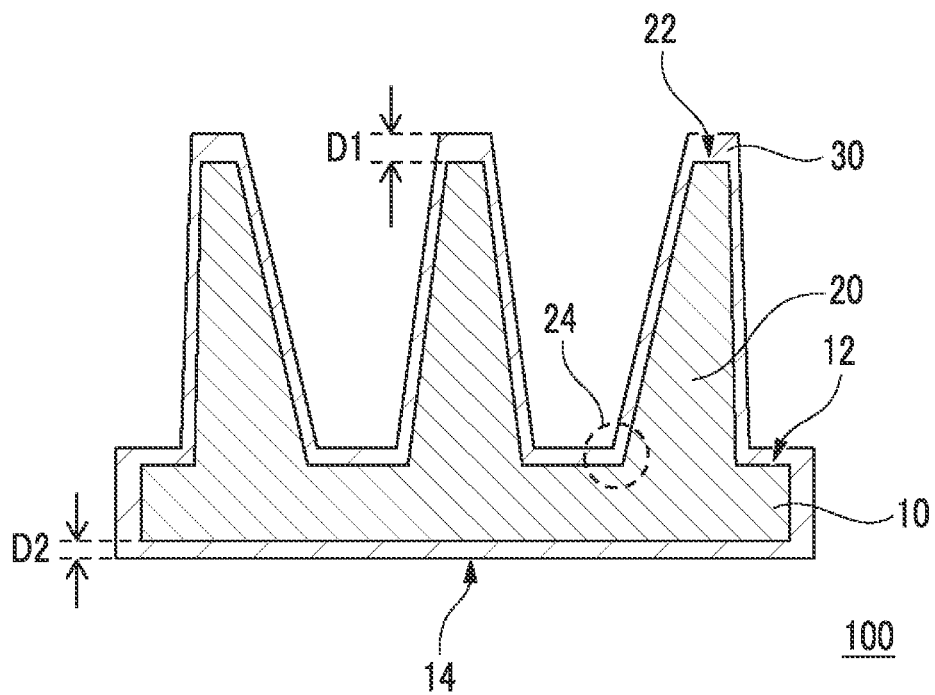

FIGS. 1A and 1B are schematic diagrams showing the summary of a biomedical electrode 100 according to the embodiment, in which FIG. 1A is a perspective view and FIG. 1B is a cross-sectional view taken along line A-A of FIG. 1A.

A biomedical electrode 100 in FIGS. 1A and 1B includes a plate-shaped support portion 10, an elastic pillar portion (pillar portion 20), and a conductive resin layer 30.

The plate-shaped support portion 10 is formed of an insulating silicone rubber, in which the plurality of pillar portion 20 are provided on a first surface 12.

The conductive resin layer 30 is formed of a conductive silicone rubber and is formed to cover at least a surface of a distal end 22 (a part of a distal end portion) of the pillar portion 20.

When the distal end 22 of the biomedical electrode 100 comes into contact with a measurement target, a bioelectric signal detected by the pillar portion 20 through the conductive resin layer 30 can be transmitted to an external connection portion 110 (connector) provided in the plate-shaped support portion 10. The bioelectric signal detected by the biomedical electrode 100 can be transmitted to an external apparatus through the connector.

The shape of the plate-shaped support portion 10 in a top view may be, for example, a substantially circular shape such as an elliptical shape or a perfect circular shape or may be a substantially polygonal shape such as a square shape, a rectangular shape, a pentagonal shape, or a hexagonal shape. Roundness (R) may be imparted to a corner portion of the polygonal shape.

Here, the top view represents a state where the biomedical electrode 100 is seen from the first surface 12 of the plate-shaped support portion 10 from which the pillar portion 20 protrudes.

The first surface 12 of the plate-shaped support portion 10 may be configured to be flat or have a curved surface that is curved outward. A second surface 14 of the plate-shaped support portion 10 may have a structure that can be connected to the connector. For example, an electrode that can be electrically connected to the connector may be buried in the second surface 14 opposite to the first surface 12 in a state where a part of the second surface 14 is exposed.

The plate-shaped support portion 10 may be configured as a member integrated with the pillar portion 20. That is, the plate-shaped support portion 10 may be integrally formed of the same resin material as the plurality of pillar portions 20. For example, by molding a curable elastomer composition such as a silicone rubber-based curable composition described below, the plate-shaped support portion 10 and the plurality of pillar portion 20 may be seamlessly bonded to each other to obtain a compact. As a result, an elastic compact having excellent flexibility and strength can be realized.

Each of the plate-shaped support portion 10 and the pillar portion 20 may be formed of an insulating elastic member (compact) including an insulating silicone rubber without including a conductive filler.

It is preferable that the plurality of pillar portion 20 are arranged to surround a center portion 50 of the first surface 12 of the plate-shaped support portion 10. In other words, the plurality of pillar portion 20 are arranged along an outer peripheral edge of the plate-shaped support portion 10. As a result, the followability of the pillar portion 20 to a living body can be improved.

In a case where the shape of the plate-shaped support portion 10 in a top view is a substantially circular shape, the plurality of pillar portion 20 may be arranged on the first surface 12 in a substantially circular shape or a substantially elliptical shape. The pillar portion 20 may be arranged to configure one or more concentric circles around the center portion 50.

The center portion 50 of the plate-shaped support portion 10 can be positioned at substantially equal distances from the distal ends 22 of the plurality of pillar portion 20 present on the same circumference.

The pillar portion 20 may be formed in a substantially pillar shape, a substantially prismatic shape, a substantially conical shape, a substantially pyramid shape, a substantially truncated conical shape, or a substantially truncated pyramid shape. In particular, a structure having a tapered shape such as a conical shape or a pyramid shape is preferable from the viewpoint of manufacturing stability, and a substantially truncated conical shape is preferable from the viewpoint of measurement stability. The truncated conical pillar portion 20 is configured such that the diameter decreases from a connection portion (base end 24) to the plate-shaped support portion 10 toward the distal end 22 side. A shape of the distal end 22 in a top view may be, for example, substantially circular or substantially polygonal.

Figure 3A:
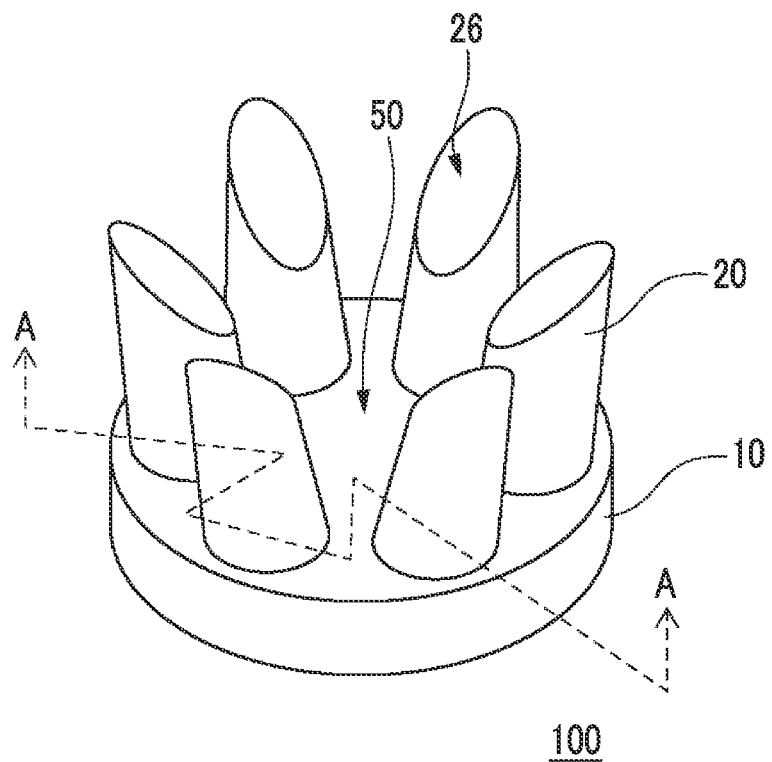

As shown in FIG. 3A, a distal end portion 26 of the pillar portion 20 may include an inclined surface 28.

That is, the distal end portions 26 of the plurality of pillar portion 20 may have the inclined surface 28 that is configured such that the height of the pillar portion 20 on the outside is higher than that on the inside in a cross-sectional view in a direction passing through the outside from the inside of each of the pillar portions 20, for example, in a radial direction. The inclined surface 28 of each of the pillar portion 20 may be configured to face the center portion 50 of the plate-shaped support portion 10. When the pillar portion 20 and a measurement target come into contact with each other, the inclined surface 28 can follow a measurement surface of the measurement target. Therefore, a variation in contact area can be suppressed.

The shape of the inclined surface 28 in a top view may be, for example, a substantially elliptical shape. This substantially elliptical shape may have a major axis of in a radial direction of a substantially circumference where the pillar portion 20 is arranged. The followability to the measurement surface can be improved.

Figure 3B:
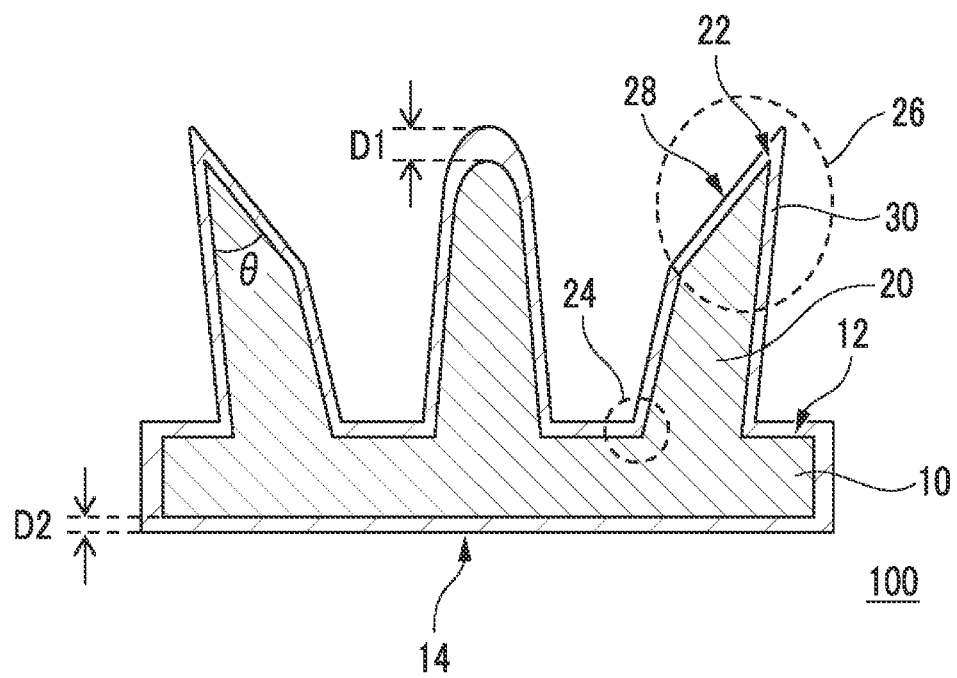

As shown in FIG. 3B, in a cross-sectional view passing through the outside from the inside of each of the pillar portions 20, an inclination angle θ of the inclined surface 28 refers to an angle between an outside surface of the pillar portion 20 and the inclined surface 28.

The inclination angle θ of the inclined surface 28 is, for example, 10 to 89 degrees, preferably 15 degrees to 80 degrees, more preferably 20 degrees to 60 degrees, and still more preferably 25 degrees to 50 degrees. By adjusting the inclination angle θ of the inclined surface 28 to be the lower limit value or more, the followability to the measurement surface can be improved. By adjusting the inclination angle θ of the inclined surface 28 to be the upper limit value or less, a variation in the deformed state can be suppressed.

Roundness (R) may be imparted to a corner portion where the inclined surface 28 of the pillar portion 20 and the side surface of the pillar portion 20 intersect each other. In particular, by imparting roundness to the corner portion of the inclined surface 28 and the outside surface, discomfort during the contact with a measurement target can be suppressed, and a variation in the deformation state of the pillar portion 20 can be further suppressed.

The pillar portion 20 may have a structure in which the center is eccentric with respect to the direction perpendicular to the first surface 12 of the plate-shaped support portion 10. From the viewpoint of manufacturing stability, it is preferable that the central axis of the pillar portion 20 having the eccentric structure is inclined from the center portion 50 of the plate-shaped support portion 10 toward the outside.

The inclination of the central axis of the pillar portion 20 refers to an outside angle (acute angle) between the central axis of the pillar portion 20 and the first surface 12 (surface) of the plate-shaped support portion 10 in a cross-sectional view passing through the center portion 50 and the center portion of the pillar portion 20 from the inside toward the outside of each of the pillar portion 20 with respect to the center portion 50.

The inclination of the central axis of the pillar portion 20 is, for example, 45 degrees to 90 degrees, preferably 50 degrees to 88 degrees, and more preferably 60 degrees to 85 degrees. In the above-described numerical range, releasability from a mold can be improved.

Figure 4A:
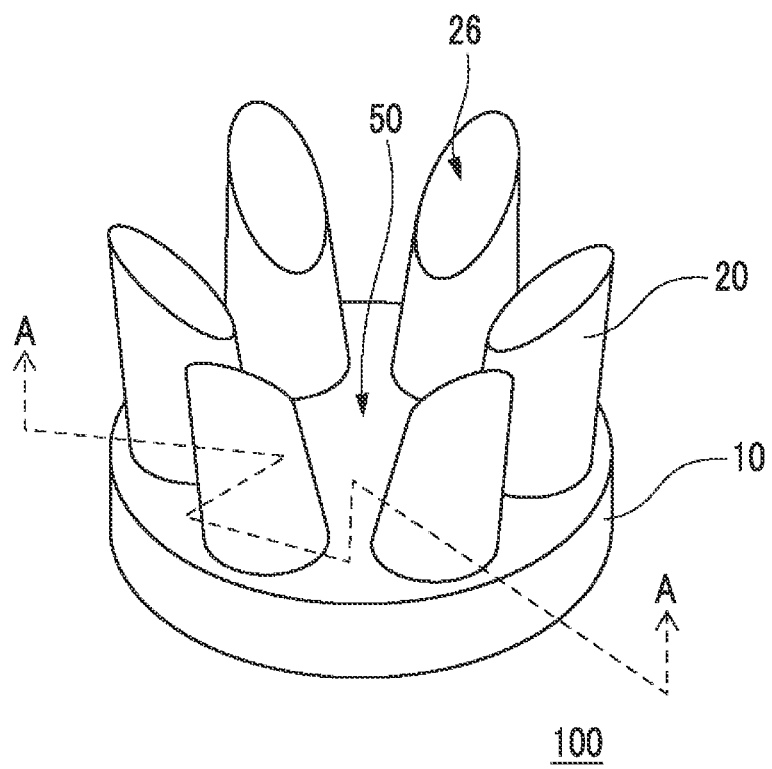
Figure 4B:
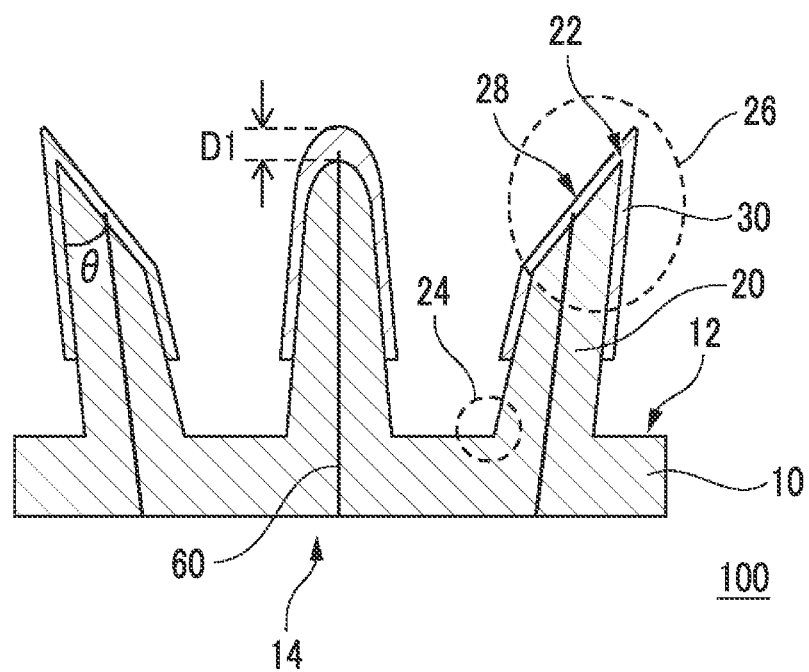

In addition, as shown in FIG. 4B, the pillar portion 20 may include a conductive wire 60. The conductive wire 60 is electrically connected to the conductive resin layer 30 and is arranged in the elastic pillar portion 20 from the distal end 22 side toward the base end 24 side.

When the distal end portion of the biomedical electrode 100 comes into contact with a measurement target, a bioelectric signal detected by the pillar portion 20 through the conductive resin layer 30 and the conductive wire 60 can be transmitted to the connector (external connection portion 110) provided in the plate-shaped support portion 10. The bioelectric signal detected by the biomedical electrode 100 can be transmitted to an external apparatus through the connector.

As the conductive wire 60, a well-known material can be used. For example, the conductive wire 60 can be formed of conductive fiber. As the conductive fiber, one or more selected from the group consisting of metal fiber, metal-coated fiber, carbon fiber, conductive polymer fiber, conductive polymer-coated fiber, and conductive paste-coated fiber can be used. Among these, one kinds may be used alone, or two or more kinds may be used in combination.

The metal material of the metal fiber and the metal-coated fiber is not particularly limited as long as it has conductivity. Examples of the metal material include copper, silver, gold, nickel, tin, lead, zinc, bismuth, antimony, stainless steel, aluminum, and an alloy thereof. Among these, one kinds may be used alone, or two or more kinds may be used in combination. Among these, from the viewpoint of conductivity, silver can be used. In addition, it is preferable that the metal material does not include metal such as chromium that imposes burden on the environment.

The fiber material of the metal-coated fiber, the conductive polymer-coated fiber, or the conductive paste-coated fiber is not particularly limited and may be any one of synthetic fiber, semisynthetic fiber, or natural fiber. Among these, for example, polyester, nylon, polyurethane, silk, or cotton is preferably used. Among these, one kinds may be used alone, or two or more kinds may be used in combination.

Examples of the carbon fiber include a PAN-based carbon fiber and a pitch-based carbon fiber.

As the conductive polymer material of the conductive polymer fiber or the conductive polymer-coated fiber, for example, polythiophene, polypyrrole, polyaniline, polyacetylene, polyphenylene vinylene, polynaphthalene, a mixture of the conductive polymer and the binder resin, for example, a derivatives thereof, or an aqueous solution of the conductive polymer PEDOT-PSS ((3,4-ethylenedioxythiophene)-poly(styrene sulfonate)) is used.

The resin material in the conductive paste of the conductive paste-coated fiber is not particularly limited and preferably has elasticity. For example, the resin material includes one or more selected from the group consisting of silicone rubber, urethane rubber, fluorine rubber, nitrile rubber, acrylic rubber, styrene rubber, chloroprene rubber, and ethylene propylene rubber. Among these, one kinds may be used alone, or two or more kinds may be used in combination.

The conductive filler in the conductive paste of the conductive paste-coated fiber is not particularly limited, and a well-known conductive material may be used. For example, the conductive filler may include one or more selected from the group consisting of metal particles, metal fiber, metal-coated fiber, carbon black, acetylene black, graphite, carbon fiber, carbon nanotube, a conductive polymer, conductive polymer-coated fiber, and metal nanowire.

The metal forming the conductive filler is not particularly limited. For example, the metal may include at least one or two or more among copper, silver, gold, nickel, tin, lead, zinc, bismuth, antimony, silver or silver chloride, and alloys thereof. In particular, silver or copper is preferable from the viewpoint of high conductivity or high availability.

The conductive wire 60 may be formed of twisted yarn obtained by twisting a plurality of linear conductive fibers. As a result, disconnection of the conductive wire 60 during deformation can be suppressed.

In this specification, the coating of the conductive fiber represents not only that the outer surface of the fiber material is covered with the conductive fiber but also that gaps between fibers in twisted yarn obtained by twisting single fibers are impregnated with metal, the conductive polymer, or the conductive paste such that each of the single fibers forming the twisted yarn is coated with the conductive fiber.

The tensile elongation at break of the conductive wire 60 is, for example, 1% or higher and 50% or lower and preferably 1.5% or higher and 45% or lower. In the numerical range, excessive deformation of the pillar portion 20 can be suppressed while suppressing break during deformation.

In a cross-sectional view passing through the center portion 50 and the pillar portion 20, the length of the pillar portion 20 from the base end 24 connected to the plate-shaped support portion 10 to the distal end 22 can be configured to be longer than the width of the pillar portion in the base end 24. As a result, the arrangement density of the pillar portion 20 can be improved. In addition, the pillar portion 20 can be suppressed from coming into contact with each other during deformation.

The conductive resin layer 30 may have any configuration as long as it can be electrically connected to the connector connected to the second surface 14 of the plate-shaped support portion 10.

The conductive resin layer 30 may be configured to cover the entirety of at least the surface of the distal end 22 of the pillar portion 20, to cover the entirety of a surface from the distal end 22 of the pillar portion 20 to a middle portion of the base end 24, or to cover the entirety of the surface of the pillar portion 20. In this case, the biomedical electrode 100 includes the conductive wire 60 that is electrically connected to the conductive resin layer 30 and is arranged inside the pillar portion 20 from the distal end side toward the base end side. A material or an arrangement position of the conductive wire 60 is not particularly limited as long as the conductive wire is conductive. As a result, in the biomedical electrode 100, the bioelectrical potential can be measured through the conductive wire 60.

Alternatively, the conductive resin layer 30 may be configured to cover the first surface 12 or the second surface 14 of the plate-shaped support portion 10, or to cover the surface of the plate-shaped support portion 10 and the surface of the pillar portion 20. In this case, the conductive resin layer 30 may be configured to cover at least the surface of the plate-shaped support portion 10 on the first surface 12 side continuously from the surface of the pillar portion 20 or may be configured to cover a part of the first surface 12 or the second surface 14. As a result, in the biomedical electrode 100, the bioelectrical potential can be measured through the conductive resin layer 30.

The conductive resin layer 30 is formed of a conductive silicone rubber including a conductive filler and a silicone rubber. For example, a conductive solution (conductive silicone rubber-based curable composition) in which a conductive filler is added to an insulating silicone rubber-based curable composition not including a conductive filler described below is applied to the above-described compact such that the conductive resin layer 30 can be formed. By using the same silicone rubber material as the silicone rubber forming the plate-shaped support portion 10 or the pillar portion 20, the adhesion of the conductive resin layer 30 can be improved.

As the conductive filler, a well-known conductive material may be used. The conductive filler may include one or more selected from the group consisting of metal particles, metal fiber, metal-coated fiber, carbon black, acetylene black, graphite, carbon fiber, carbon nanotube, a conductive polymer, conductive polymer-coated fiber, and metal nanowire.

The metal forming the conductive filler is not particularly limited. For example, the metal may include at least one or two or more among copper, silver, gold, nickel, tin, lead, zinc, bismuth, antimony, silver or silver chloride, and alloys thereof. In particular, silver or copper is preferable from the viewpoint of high conductivity or high availability.

The lower limit value of the content of the conductive filler is, for example, 30 mass % or higher, preferably 35 mass % or higher, and more preferably 40 mass % or higher with respect to 100 mass % of the silicone rubber in the conductive resin layer 30. As a result, even in the case of a thin film, the transmission performance of a bioelectric signal can be improved. On the other hand, the upper limit value of the content of the conductive filler is, for example, 90 mass % or lower, preferably 85 mass % or lower and more preferably 80 mass % or lower with respect to 100 mass % of the silicone rubber in the conductive resin layer 30. As a result, the durability of the conductive resin layer 30 for the deformation of the pillar portion 20 can be improved.

The lower limit value of the thickness of the conductive resin layer 30 is, for example, 5 µm or more, preferably 8 µm or more, and more preferably 10 µm or more. As a result, the durability during repeated use can be improved. On the other hand, the upper limit value of the thickness of the conductive resin layer 30 is, for example, 200 µm or less, preferably 150 µm or less, more preferably 100 µm or less, and still more preferably 50 µm or less. As a result, the deformation easiness of the pillar portion 20 can be maintained. In addition, by reducing the thickness of the layer, a variation from a desired value can be suppressed regarding the rubber hardness A of the pillar portion 20. In a cross-sectional view of the pillar portion 20, the thickness of the conductive resin layer 30 on at least a part of the distal end 22 or the side surface of the pillar portion 20 is preferably in the numerical range.

Regarding the thickness of the conductive resin layer 30, a thickness D1 on the surface of the distal end 22 of the pillar portion 20 may be configured to be thicker than a thickness D2 on the second surface 14 of the plate-shaped support portion 10. For example, after applying the above-described conductive solution, a part of the pillar portion 20 coated with the conductive resin layer 30 may be dipped (dip coating) in a paste-like conductive solution. As a result, while reducing the thickness of the entire conductive resin layer 30, the thickness of the distal end 22 of the pillar portion 20 or the thickness of a portion from the distal end 22 to a predetermined portion (for example, ½, ⅓, or ¼ of the entire pillar portion 20) can be made to be relatively thick. It is preferable that this thick region is provided in the entirety of the distal end portion of the pillar portion 20 in the circumferential direction. As a result, peeling of the conductive resin layer 30 in the distal end portion can be suppressed, and damages such as disconnection of the pillar portion 20 can be suppressed. Therefore, the durability of the biomedical electrode 100 can be improved.

In the embodiment, a type A durometer hardness of a surface of the pillar portion 20 (elastic pillar portion) that is measured at 37° C. according to JIS K 6253 (1997) is adopted as the rubber hardness A.

As the measurement target of the rubber hardness A, a method of using the pillar portion 20, a method of using the plate-shaped support portion 10 when the pillar portion 20 and the plate-shaped support portion 10 are formed as an integrated member, or a method of using a silicone rubber that forms the pillar portion 20 or the plate-shaped support portion 10 can be adopted. In addition, when the conductive resin layer 30 is a thin layer and thus has little effect on the rubber hardness A, the pillar portion 20 or the plate-shaped support portion 10 having a surface on which the conductive resin layer 30 is formed may be used as a measurement target. A specimen may be prepared from the pillar portion 20 or the plate-shaped support portion 10 and may be used as a measurement target (sample). The thickness of a plurality of specimens that are laminated may be adopted as a sample thickness. Even when the distance from a press needle to a specimen end is less than 12 mm, the distance is allowable as long as it is large to some extent.

The lower limit of the rubber hardness A is higher than 35 and preferably 36 or higher. As a result, the contact resistance is low, and the brain wave acquisition ratio is improved. On the other hand, the upper limit of the rubber hardness A is 65 or lower, preferably 53 or lower, and more preferably 50 or lower. As a result, the contact resistance can be set to be low. In addition, when coming into contact with a measurement portion, the pillar portion 20 can be easily deformed in a state where it follows the shape of the measurement portion. Therefore, the wearability of a subject (user) is improved, and discomfort during repeated use can be suppressed.

Here, the silicone rubber-based curable composition will be described.

The silicone rubber can be formed of a cured product of the silicone rubber-based curable composition. A step of curing the silicone rubber-based curable resin composition is performed by heating (primary curing) the composition, for example, at 100° C. to 250° C. for 1 to 30 minutes and post-baking (secondary curing) the heated composition at 100° C. to 200° C. for 1 to 4 hours.

The insulating silicone rubber is a silicone rubber not including a conductive filler, and the conductive silicone rubber is a silicone rubber including a conductive filler.

The silicone rubber-based curable composition according to the embodiment may include a vinyl group-containing organopolysiloxane (A). The vinyl group-containing organopolysiloxane (A) is a polymer including the silicone rubber-based curable composition according to the embodiment as a main element.

The insulating silicone rubber-based curable composition and the conductive silicone rubber-based curable composition may include the same kind of vinyl group-containing linear organopolysiloxanes. The same kind of vinyl group-containing linear organopolysiloxanes only have to include at least a vinyl group having the same functional group and to be linear, and may have different vinyl group contents or molecular weight distributions in the molecule, or different addition amounts thereof.

The insulating silicone rubber-based curable composition and the conductive silicone rubber-based curable composition may include different kinds of vinyl group-containing organopolysiloxanes.

The vinyl group-containing organopolysiloxane (A) may include a vinyl group-containing linear organopolysiloxane (A1) having a linear structure.

The vinyl group-containing linear organopolysiloxane (A1) has a linear structure and includes a vinyl group, in which the vinyl group functions as a crosslinking point during curing.

The content of the vinyl group in the vinyl group-containing linear organopolysiloxane (A1) is not particularly limited. For example, the vinyl group-containing linear organopolysiloxane (A1) includes two or more vinyl groups in the molecule, and the content thereof is preferably 15 mol % or lower and more preferably 0.01% to 12 mol %. As a result, the content of the vinyl group in the vinyl group-containing linear organopolysiloxane (A1) can be optimized, and a network between the respective components can be reliably formed. In the embodiment, a range represented by "to" includes numerical values of both ends.

In this specification, the content of the vinyl group represents mol % of a vinyl group-containing siloxane unit with respect to 100 mol % of all the units forming the vinyl group-containing linear organopolysiloxane (A1). In this case, it is assumed that one vinyl group is present for each vinyl group-containing siloxane unit.

In addition, the polymerization degree of the vinyl group-containing linear organopolysiloxane (A1) is not particularly limited and is, for example, preferably in a range of about 1000 to 10000 and more preferably in a range of about 2000 to 5000. The polymerization degree can be obtained as, for example, a number average polymerization degree (number average molecular weight) in terms of polystyrene in GPC (gel permeation chromatography) in which chloroform is used as an eluent.

Further, the specific gravity of the vinyl group-containing linear organopolysiloxane (A1) is not particularly limited and is preferably in a range of about 0.9 to 1.1.

By using the vinyl group-containing linear organopolysiloxane (A1) having the polymerization degree and the specific gravity in the above-described ranges, the heat resistance, flame retardancy, chemical stability, and the like of the obtained silicone rubber can be improved.

It is preferable that the vinyl group-containing linear organopolysiloxane (A1) has a structure represented by the following Formula (1).

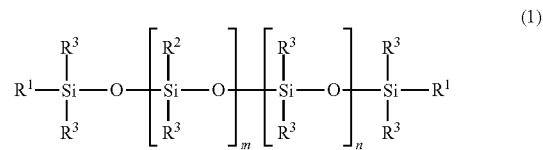

In Formula (1), $R^1$ represents a substituted or unsubstituted alkyl group, alkenyl group, or aryl group having 1 to 10 carbon atoms, or a hydrocarbon group including a combination thereof. Examples of the alkyl group having 1 to 10 carbon atoms include a methyl group, an ethyl group, and a propyl group. In particular, a methyl group is preferable. Examples of the alkenyl group having 1 to 10 carbon atoms include a vinyl group, an allyl group, and a butenyl group. In particular, a vinyl group is preferable. Examples of the aryl group having 1 to 10 carbon atoms include a phenyl group.

In addition, $R^2$ represents a substituted or unsubstituted alkyl group, alkenyl group, or aryl group having 1 to 10 carbon atoms, or a hydrocarbon group including a combination thereof. Examples of the alkyl group having 1 to 10 carbon atoms include a methyl group, an ethyl group, and a propyl group. In particular, a methyl group is preferable. Examples of the alkenyl group having 1 to 10 carbon atoms include a vinyl group, an allyl group, and a butenyl group. Examples of the aryl group having 1 to 10 carbon atoms include a phenyl group.

In addition, $R^3$ represents a substituted or unsubstituted alkyl group or aryl group having 1 to 8 carbon atoms, or a hydrocarbon group including a combination thereof. Examples of the alkyl group having 1 to 8 carbon atoms include a methyl group, an ethyl group, and a propyl group. In particular, a methyl group is preferable. Examples of the aryl group having 1 to 8 carbon atoms include a phenyl group.

Further, examples of a substituent of $R^1$ and $R^2$ in Formula (1) include a methyl group and a vinyl group. Examples of a substituent of $R^3$ include a methyl group.

In Formula (1), a plurality of $R^1$'s may be independent from each other and may be the same as or different from each other. Further, the same can be applied to $R^2$ and $R^3$.

Further, m and n each independently represent the number of repeating units forming the vinyl group-containing linear organopolysiloxane (A1) represented by Formula (1), m represents an integer of 0 to 2000, and n represents an integer of 1000 to 10000. m represents preferably 0 to 1000, and n represents preferably 2000 to 5000.

In addition, examples of a specific structure of the vinyl group-containing linear organopolysiloxane (A1) represented by Formula (1) include a structure represented by the following Formula (1-1).

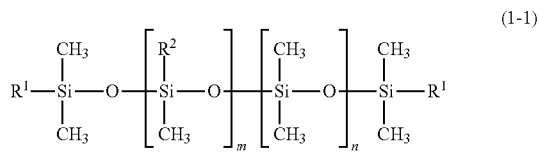

(1-1)

In Formula (1-1), $R^1$ and $R^2$ each independently represent a methyl group or a vinyl group, and at least one of $R^1$ or $R^2$ represents a vinyl group.

Further, it is preferable that as the vinyl group-containing linear organopolysiloxane (A1), a first vinyl group-containing linear organopolysiloxane (A1-1) having two or more vinyl groups in the molecule in which the vinyl group content is 0.4 mol % or lower; or a second vinyl group-containing linear organopolysiloxane (A1-2) in which the vinyl group content is 0.5 to 15 mol % is included. By using the first vinyl group-containing linear organopolysiloxane (A1-1) having the general vinyl group content and the second vinyl group-containing linear organopolysiloxane (A1-2) having the higher vinyl group in combination as raw rubber that is a material of the silicone rubber, the vinyl groups can be distributed, and a structure of the crosslinking density in the crosslinked network of the silicone rubber can be more effectively formed. As a result, the tear strength of the silicone rubber can be more effectively improved.

Specifically, as the vinyl group-containing linear organopolysiloxane (A1), for example, the first vinyl group-containing linear organopolysiloxane (A1-1) having two or more of a unit in which $R^1$ in Formula (1-1) represents a vinyl group and/or a unit in which $R^2$ in Formula (1-1) represents a vinyl group in the molecule and the content is 0.4 mol % or less, or the second vinyl group-containing linear organopolysiloxane (A1-2) including 0.5 to 15 mol % of a unit in which $R^1$ in Formula (1-1) represents a vinyl group and/or a unit in which $R^2$ in Formula (1-1) represents a vinyl group is preferably used.

In addition, in the first vinyl group-containing linear organopolysiloxane (A1-1), the vinyl group content is preferably 0.01 to 0.2 mol %. In addition, in the second vinyl group-containing linear organopolysiloxane (A1-2), the vinyl group content is preferably 0.8 to 12 mol %.

Further, in a case where the first vinyl group-containing linear organopolysiloxane (A1-1) and the second vinyl group-containing linear organopolysiloxane (A1-2) are mixed in combination, the ratio between (A1-1) and (A1-2) is not particularly limited. For example, the weight ratio (A1-1):(A1-2) is preferably 50:50 to 95:5 and more preferably 80:20 to 90:10.

As each of the first and second vinyl group-containing linear organopolysiloxanes (A1-1) and (A1-2), only one kind may be used, or two or more kinds may be used in combination.

In addition, the vinyl group-containing organopolysiloxane (A) may include a vinyl group-containing branched organopolysiloxane (A2) having a branched structure.

<<Organohydrogen Polysiloxane (B)>>

The silicone rubber-based curable composition according to the embodiment may include a crosslinking agent. The crosslinking agent may include an organohydrogen polysiloxane (B).

The organohydrogen polysiloxane (B) is classified into a linear organohydrogen polysiloxane (B1) having a linear structure and a branched organohydrogen polysiloxane (B2) having a branched structure and may include either or both of (B1) and (B2).

The insulating silicone rubber-based curable composition and the conductive silicone rubber-based curable composition may include the same kind of crosslinking agents. The same kind of crosslinking agents only have to at least a common structure such as a linear structure or a branched structure, and may have different molecular weight distributions in the molecule, different functional groups, or different addition amounts thereof.

The insulating silicone rubber-based curable composition and the conductive silicone rubber-based curable composition may further include different kinds of crosslinking agents.

The linear organohydrogen polysiloxane (B1) is a polymer that has a linear structure and a structure (≡Si—H) in which hydrogen is directly bonded to Si and that is obtained by a hydrosilylation reaction of the vinyl group in the vinyl group-containing organopolysiloxane (A) and a vinyl group in a component mixed in the silicone rubber-based curable composition to crosslink the components.

The molecular weight of the linear organohydrogen polysiloxane (B1) is not particularly limited. For example, the weight average molecular weight is preferably 20000 or lower and more preferably 1000 or higher and 10000 or lower.

The weight average molecular weight of the linear organohydrogen polysiloxane (B1) can be measured in terms of polystyrene in GPC (gel permeation chromatography) in which chloroform is used as an eluent.

In addition, it is preferable that, typically, the linear organohydrogen polysiloxane (B1) does not have a vinyl group As a result, the crosslinking reaction in the molecule of the linear organohydrogen polysiloxane (B1) can be reliably prevented from progressing.

It is preferable to use the linear organohydrogen polysiloxane (B1), for example, having a structure represented by the following Formula (2).

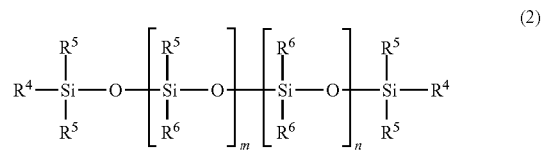

(2)

In Formula (2), $R^4$ represents a substituted or unsubstituted alkyl group, alkenyl group, or aryl group having 1 to 10 carbon atoms, a hydrocarbon group including a combination thereof, or a hydride group. Examples of the alkyl group having 1 to 10 carbon atoms include a methyl group, an ethyl group, and a propyl group. In particular, a methyl group is preferable. Examples of the alkenyl group having 1 to 10 carbon atoms include a vinyl group, an allyl group, and a butenyl group. Examples of the aryl group having 1 to 10 carbon atoms include a phenyl group.

In addition, $R^5$ represents a substituted or unsubstituted alkyl group, alkenyl group, or aryl group having 1 to 10 carbon atoms, a hydrocarbon group including a combination thereof, or a hydride group. Examples of the alkyl group having 1 to 10 carbon atoms include a methyl group, an ethyl group, and a propyl group. In particular, a methyl group is preferable. Examples of the alkenyl group having 1 to 10 carbon atoms include a vinyl group, an allyl group, and a butenyl group. Examples of the aryl group having 1 to 10 carbon atoms include a phenyl group.

In Formula (2), a plurality of $R^4$'s may be independent from each other and may be the same as or different from each other. The same can be applied to $R^5$. In this case, at least two or more among a plurality of $R^4$'s and a plurality of $R^5$'s represent a hydride group.

In addition, $R^6$ represents a substituted or unsubstituted alkyl group or aryl group having 1 to 8 carbon atoms, or a hydrocarbon group including a combination thereof. Examples of the alkyl group having 1 to 8 carbon atoms include a methyl group, an ethyl group, and a propyl group. In particular, a methyl group is preferable. Examples of the aryl group having 1 to 8 carbon atoms include a phenyl group. A plurality of $R^6$'s may be independent from each other and may be the same as or different from each other.

Examples of a substituent of $R^4$, $R^5$, and $R^6$ in Formula (2) include a methyl group and a vinyl group. From the viewpoint of preventing a crosslinking reaction in the molecule, a methyl group is preferable.

Further, m and n each independently represent the number of repeating units forming the linear organohydrogen polysiloxane (B1) represented by Formula (2), m represents an integer of 2 to 150, and n represents an integer of 2 to 150. It is preferable that m represents an integer of 2 to 100 and n represents an integer of 2 to 100.

As the linear organohydrogen polysiloxane (B1), only one kind may be used alone, or two or more kinds may be used in combination.

The branched organohydrogen polysiloxane (B2) has a branched structure and thus is a component that largely contributes to the formation of a structure of the crosslinking density in the silicone rubber system by forming a region having a high crosslinking density. In addition, as in the linear organohydrogen polysiloxane (B1), the branched organohydrogen polysiloxane (B2) is a polymer that a structure (≡Si—H) in which hydrogen is directly bonded to Si and that is obtained by a hydrosilylation reaction of the vinyl group in the vinyl group-containing organopolysiloxane (A) and a vinyl group in a component mixed in the silicone rubber-based curable composition to crosslink the components.

In addition, the specific gravity of the branched organohydrogen polysiloxane (B2) is in a range of 0.9 to 0.95.

Further, it is preferable that, typically, the branched organohydrogen polysiloxane (B2) does not have a vinyl group. As a result, the crosslinking reaction in the molecule of the branched organohydrogen polysiloxane (B2) can be reliably prevented from progressing.

In addition, it is preferable that the branched organohydrogen polysiloxane (B2) is represented by Average Compositional Formula (c) described below.

$(H_a(R^7)_{3-a}SiO_{1/2})_m(SiO_{4/2})_n$     Average Compositional Formula (c)

(In Formula (c), $R^7$ represents a monovalent organic group, a represents an integer of 1 to 3, m represents the number of $H_a(R^7)_{3-a}SiO_{1/2}$ units, and n represents the number of $SiO_{4/2}$.)

In Formula (c), $R^7$ represents a monovalent organic group, and represents preferably a substituted or unsubstituted alkyl group or aryl group having 1 to 10 carbon atoms, or a hydrocarbon group including a combination thereof. Examples of the alkyl group having 1 to 10 carbon atoms include a methyl group, an ethyl group, and a propyl group.

In particular, a methyl group is preferable. Examples of the aryl group having 1 to 10 carbon atoms include a phenyl group.

In Formula (c), a represents the number of hydride groups (hydrogen atoms directly bonded to Si) which is an integer of 1 to 3 and preferably 1.

In addition, in Formula (c), m represents the number of $H_a(R^7)_{3-a}SiO_{1/2}$ units, and n represents the number of $SiO_{4/2}$.

The branched organohydrogen polysiloxane (B2) has a branched structure. The linear organohydrogen polysiloxane (B1) and the branched organohydrogen polysiloxane (B2) are different from each other in that whether the structure is linear or branched. A ratio of the number (R/Si) of alkyl groups R bonded to Si to the number of Si that is 1 is 1.8 to 2.1 in the linear organohydrogen polysiloxane (B1) and is 0.8 to 1.7 in the branched organohydrogen polysiloxane (B2).

Since the branched organohydrogen polysiloxane (B2) has a branched structure, the amount of residues is 5% or higher, for example, during heating to 1000° C. at a temperature increase rate of 10° C./min in a nitrogen atmosphere. On the other hand, since the linear organohydrogen polysiloxane (B1) is linear, the amount of residues after heating under the above-described conditions is substantially zero.

In addition, specific examples of the branched organohydrogen polysiloxane (B2) include a branched organohydrogen polysiloxane (B2) having a structure represented by the following Formula (3).

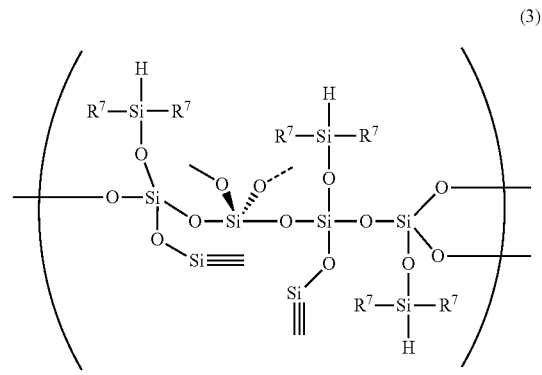

(3)

In Formula (3), $R^7$ represents a substituted or unsubstituted alkyl group or aryl group having 1 to 8 carbon atoms, a hydrocarbon group including a combination thereof, or a hydrogen atom. Examples of the alkyl group having 1 to 8 carbon atoms include a methyl group, an ethyl group, and a propyl group. In particular, a methyl group is preferable. Examples of the aryl group having 1 to 8 carbon atoms include a phenyl group. Examples of a substituent of $R^7$ include a methyl group.

In Formula (3), a plurality of $R^7$'s may be independent from each other and may be the same as or different from each other.

In addition, in Formula (3), "—O—Si≡" represents that Si has a branched structure that spreads three-dimensionally.

As the branched organohydrogen polysiloxane (B2), only one kind may be used alone, or two or more kinds may be used in combination.

In addition, in each of the linear organohydrogen polysiloxane (B1) and the branched organohydrogen polysiloxane (B2), the amount of hydrogen atoms (hydride groups) directly bonded to Si is not particularly limited. In the silicone rubber-based curable composition, the total amount of hydride groups in the linear organohydrogen polysiloxane (B1) and the branched organohydrogen polysiloxane (B2) is preferably 0.5 to 5 mol and more preferably 1 to 3.5 mol with respect to 1 mol of vinyl group in the vinyl group-containing linear organopolysiloxane (A1). As a result, a crosslinked network can be reliably formed between the linear organohydrogen polysiloxane (B1) and the branched organohydrogen polysiloxane (B2), and the vinyl group-containing linear organopolysiloxane (A1).

<<Silica Particles (C)>>

The silicone rubber-based curable composition according to the embodiment includes a non-conductive filler. The non-conductive filler may optionally include silica particles (C). As a result, the hardness or mechanical strength of the elastomer can be improved.

The insulating silicone rubber-based curable composition and the conductive silicone rubber-based curable composition may include the same kind of non-conductive fillers. The same kind of non-conductive fillers only have to include at least a common constituent material, and may have different particle sizes, specific surface areas, surface treatment agents, or addition amounts thereof.

The insulating silicone rubber-based curable composition and the conductive silicone rubber-based curable composition may further include different kinds of silane coupling agents.

The silica particles (C) are not particularly limited. For example, fumed silica, pyrogenic silica, or precipitated silica is used. Among these, one kinds may be used alone, or two or more kinds may be used in combination.

The specific surface area of the silica particles (C) measured using, for example, a BET method is, for example, preferably 50 to 400 m$^2$/g and more preferably 100 to 400 m$^2$/g. In addition, the average primary particle size of the silica particles (C) is, for example, preferably 1 to 100 nm and more preferably about 5 to 20 nm.

By using the silica particles (C) having the specific surface area and the average particle size in the above-described range, the hardness and the mechanical strength, in particular, the tensile strength of the formed silicone rubber can be improved.

<<Silane Coupling Agent (D)>>

The silicone rubber-based curable composition according to the embodiment may include a silane coupling agent (D).

The silane coupling agent (D) may include a hydrolyzable group. The hydrolyzable group is hydrolyzed into a hydroxyl group by water, and this hydroxyl group reacts with a hydroxyl group on the silica particles (C) in a dehydration synthesis reaction. As a result, the surfaces of the silica particles (C) can be modified.

The insulating silicone rubber-based curable composition and the conductive silicone rubber-based curable composition may include the same kind of silane coupling agents. The same kind of silane coupling agents only have to include at least a common functional group, and may have different functional groups in the molecule or different addition amounts thereof.

The insulating silicone rubber-based curable composition and the conductive silicone rubber-based curable composition may further include different kinds of silane coupling agents.

In addition, the silane coupling agent (D) may include a silane coupling agent having a hydrophobic group. As a result, this hydrophobic group is added to the surfaces of the silica particles (C). Therefore, it is presumed, in the silicone rubber-based curable composition and the silicone rubber, the cohesion force between the silica particles (C) decreases (cohesion through a hydrogen bond formed by a silanol group decreases, and thus the dispersibility of the silica particles (C) in the silicone rubber-based curable composition is improved. As a result, the area of an interface between the silica particles (C) and a rubber matrix increases, and a reinforcing effect of the silica particles (C) increases. Further, it is presumed that, when the rubber matrix is deformed, the slipperiness of the silica particles (C) in the matrix is improved. By improving the dispersibility and slipperiness of the silica particles (C), the mechanical strength (for example, tensile strength or tear strength) of the silicone rubber by the silica particles (C) is improved.

Further, the silane coupling agent (D) may include a silane coupling agent having a vinyl group. As a result, a vinyl group is introduced into the surface of the silica particles (C). Therefore, when the silicone rubber-based curable composition is cured, that is, when a vinyl group in the vinyl group-containing organopolysiloxane (A) and a hydride group in the organohydrogen polysiloxane (B) react with each other in a hydrosilylation reaction such that a network (crosslinked structure) is formed, a vinyl group in the silica particles (C) gets involved with the hydrosilylation reaction with the hydride group in the organohydrogen polysiloxane (B). Therefore, the silica particles (C) are also incorporated into the network. As a result, low hardness and high modulus of the formed silicone rubber can be realized.

As the silane coupling agent (D), the silane coupling agent having a hydrophobic group and the silane coupling agent having a vinyl group can be used in combination.

Examples of the silane coupling agent (D) include a silane coupling agent represented by the following Formula (4).

$$Y_n\text{—Si—}(X)_{4-n} \quad (4)$$

In Formula (4), n represents an integer of 1 to 3. Y represents any functional group of a hydrophobic group, a hydrophilic group, or a vinyl group, when n represents 1, Y represents a hydrophobic group, and when n represents 2 or 3, at least one of Y's represents a hydrophobic group. X represents a hydrolyzable group.

The hydrophobic group is an alkyl group or aryl group having 1 to 6 carbon atoms, or a hydrocarbon group including a combination thereof. Examples of the hydrophobic group include a methyl group, an ethyl group, a propyl group, and a phenyl group. In particular, a methyl group is preferable.

In addition, examples of the hydrophilic group include a hydroxyl group, a sulfonate group, a carboxyl group, and a carbonyl group. In particular, a hydroxyl group is preferable. The hydrophilic group may be included as a functional group. However, it is preferable that the hydrophilic group is not included from the viewpoint of imparting hydrophobicity to the silane coupling agent (D).

Further, examples of the hydrolyzable group include an alkoxy group such as a methoxy group or an ethoxy group, a chloro group, and a silazane group. In particular, a silazane group is preferable from the viewpoint of high reactivity with the silica particles (C). The silane coupling agent having a silazane group as the hydrolyzable group has a structure including two structures represented by ($Y_n$—Si—) in Formula (4).

Specific examples of the silane coupling agent (D) represented by Formula (4) are as follows.

Examples of the silane coupling agent having a hydrophobic group as the functional group include: an alkoxysilane such as methyltrimethoxysilane, dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, or decyltrimethoxysilane; a chlorosilane such as methyltrichlorosilane, dimethyldichlorosilane, trimethylchlorosilane, or phenyltrichlorosilane; and hexamethyldisilazane. In particular, a silane coupling agent having a trimethylsilyl group that includes one or more selected from the group consisting of hexamethyldisilazane, trimethylchlorosilane, trimethylmethoxysilane, and trimethylethoxysilane is preferable.

Examples of the silane coupling agent having a vinyl group as the functional group include: an alkoxysilane such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, or vinylmethyldimethoxysilane; a chlorosilane such as vinyltrichlorosilane or vinylmethyldichlorosilane; and divinyltetramethyldisilazane. In particular, a silane coupling agent having a vinyl group-containing organosilyl group that includes one or more selected from the group consisting of methacryloxypropyltriethoxysilane, methacryloxypropyltrimethoxysilane, methacryloxypropylmethyldiethoxysilane, methacryloxypropylmethyldimethoxysilane, divinyltetramethyldisilazane, vinyltriethoxysilane, vinyltrimethoxysilane, and vinylmethyldimethoxysilane is preferable.

In addition, in a case where the silane coupling agent (D) includes two kinds including a silane coupling agent having a trimethylsilyl group and a silane coupling agent having a vinyl group-containing organosilyl group, it is preferable that hexamethyldisilazane is included as the silane coupling agent having a hydrophobic group and divinyltetramethyldisilazane is included as the silane coupling agent having a vinyl group.

In a case where the silane coupling agent (D1) having a trimethylsilyl group and the silane coupling agent (D2) having a vinyl group-containing organosilyl group are used in combination, a ratio between (D1) and (D2) is not particularly limited. For example, a weight ratio (D1):(D2) is 1:0.001 to 1:0.35, preferably 1:0.01 to 1:0.20, and more preferably 1:0.03 to 1:0.15. In the above-described numerical range, desired physical properties of the silicone rubber can be obtained. Specifically, a balance between the dispersibility of silica in the rubber and the crosslinkability of the rubber can be realized.

In the embodiment, the lower limit value of the content of the silane coupling agent (D) is preferably 1 mass % or higher, more preferably 3 mass % or higher, and still more preferably 5 mass % or higher with respect to 100 parts by weight of the total amount of the vinyl group-containing organopolysiloxane (A). In addition, the upper limit value of the content of the silane coupling agent (D) is preferably 100 mass % or lower, more preferably 80 mass % or lower, and still more preferably 40 mass % or lower with respect to 100 parts by weight of the total amount of the vinyl group-containing organopolysiloxane (A).

By adjusting the content of the silane coupling agent (D) to be lower limit value or higher, the adhesion between the pillar portion including the elastomer and the conductive resin layer can be improved. In addition, the improvement of the mechanical strength of the silicone rubber can be promoted. In addition, by adjusting the content of the silane coupling agent (D) to be the upper limit value or lower, the silicone rubber can be made to have appropriate mechanical properties.

<<Platinum or Platinum Compound (E)>>

The silicone rubber-based curable composition according to the embodiment may include a catalyst. The catalyst may include a platinum or platinum compound (E). The platinum or platinum compound (E) is a catalyst component that functions as a catalyst during curing. The addition amount of the platinum or platinum compound (E) is the amount of the catalyst.

The insulating silicone rubber-based curable composition and the conductive silicone rubber-based curable composition may include the same kind of catalysts. The same kind of non-conductive catalysts only have to include at least a common constituent material, and may have different compositions in the catalyst or different addition amounts thereof.

The insulating silicone rubber-based curable composition and the conductive silicone rubber-based curable composition may further include different kinds of catalysts.

As the platinum or platinum compound (E), a well-known compound can be used, and examples thereof include platinum black, silica or carbon black on which platinum is supported, chloroplatinic acid or an alcohol solution of chloroplatinic acid, a complex salt of chloroplatinic acid and olefin, and a complex salt of chloroplatinic acid and vinylsiloxane.

As the platinum or platinum compound (E), only one kind may be used alone, or two or more kinds may be used in combination.

In the embodiment, the content of the platinum or platinum compound (E) in the silicone rubber-based curable composition refers to the amount of the catalyst and can be appropriately set. Specifically, the content of platinum group metal by weight is 0.01 to 1000 ppm and preferably 0.1 to 500 ppm with respect to 100 parts by weight of the vinyl group-containing organopolysiloxane (A), the silica particles (C), and the silane coupling agent (D).

By adjusting the content of the platinum or platinum compound (E) to be the lower limit value or higher, the silicone rubber-based curable composition can be cured at an appropriate rate. In addition, by adjusting the content of the platinum or platinum compound (E) to be the upper limit value or lower, a reduction in manufacturing costs can be promoted.

<<Water (F)>>

In addition, the silicone rubber-based curable composition according to the embodiment may include water (F) in addition to the components (A) to (E).

The water (F) is a component that functions as a dispersion medium for dispersing the respective components in the silicone rubber-based curable composition and contributes to the reaction between the silica particles (C) and the silane coupling agent (D). Therefore, in the silicone rubber, the silica particles (C) and the silane coupling agent (D) can be more reliably linked to each other, and uniform properties can be exhibited as a whole.

(Other Components)

Further, the silicone rubber-based curable composition according to the embodiment may further include other components in addition to the components (A) to (F). Examples of the other components include an inorganic filler other than the silica particles (C) such as diatomaceous earth, iron oxide, zinc oxide, titanium oxide, barium oxide, magnesium oxide, cerium oxide, calcium carbonate, magnesium carbonate, zinc carbonate, glass wool, or mica, and an additive such as a reaction inhibitor, a dispersant, a pigment, a dye, an antistatic agent, an antioxidant, a flame retardant, or a thermal conductivity enhancing agent.

The conductive solution (conductive silicone rubber composition) according to the embodiment include the conductive filler and a solvent in addition to the silicone rubber-based curable composition not including the conductive filler.

As the solvent, various well-known solvents can be used. For example, a high boiling point solvent can be included. Among these, one kinds may be used alone, or two or more kinds may be used in combination.

Examples of the solvent include: an aliphatic hydrocarbon such as pentane, hexane, cyclohexane, heptane, methylcyclohexane, ethylcyclohexane, octane, decane, dodecane, or tetradecane; an aromatic hydrocarbon such as benzene, toluene, ethylbenzene, xylene, trifluoromethylbenzene, or benzotrifluoride; an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,4-dioxane, 1,3-dioxane, or tetrahydrofuran; a haloalkane such as dichloromethane, chloroform, 1,1-dichloroethane, 1,2-dichloroethane, 1,1,1-trichloroethane, or 1,1,2-trichloroethane; a carboxylic acid amid such as N,N-dimethylformamide or N,N-dimethylacetamide; and a sulfoxide such as dimethyl sulfoxide or diethyl sulfoxide. Among these, one kinds may be used alone, or two or more kinds may be used in combination.

By adjusting the solid content in the solution, the conductive solution can be made to have an appropriate viscosity for various coating methods such as spray coating or dip coating.

In addition, in a case where the conductive solution includes the conductive filler and the silica particles (C), the lower limit value of the content of the silica particles (C) in the conductive resin layer 30 is, for example, 1 mass % or higher, preferably 3 mass % or higher, and more preferably 5 mass % or higher with respect to 100 mass % of the total amount of the silica particles (C) and the conductive filler. As a result, the mechanical strength of the conductive resin layer 30 can be improved. On the other hand, the upper limit value of the content of the silica particles (C) in the conductive resin layer 30 is, for example, 20 mass % or lower, preferably 15 mass % or lower, and more preferably 10 mass % or lower with respect to 100 mass % of the total amount of the silica particles (C) and the conductive filler. As a result, a balance between the conductivity and the mechanical strength or flexibility in the conductive resin layer 30 can be realized.

By optionally heating and drying the conductive solution, the conductive silicone rubber can be obtained.

The conductive silicone rubber may be configured not to include a silicone oil. As a result, the silicone oil bleeds out to a surface of the conductive resin layer 30 such that a decrease in conductivity can be suppressed.

An example of a method of manufacturing the biomedical electrode 100 according to the embodiment may include the following steps.

First, the silicone rubber-based curable composition is molded using a mold by hot press molding to obtain a compact including the plate-shaped support portion 10 and the pillar portion 20. Next, the conductive solution is applied to a surface of the obtained compact by spray coating and is heated and dried. As a result, the conductive resin layer 30 is formed on the surfaces of the plate-shaped support portion 10 and the pillar portion 20. Optionally, the distal end portion of the pillar portion 20 may be dipped in the conductive solution and may be heated and dried.

As a result, the biomedical electrode 100 can be manufactured.

The biomedical electrode 100 according to the embodiment can detect a bioelectric signal generated form organic activities of a brain, a heart, a muscle, a nerve, or the like. The biomedical electrode 100 has flexibility and excellent wearability on a scalp, and thus can be suitably used as an electroencephalographic electrode.

The application of an electroencephalographic electrode including the biomedical electrode 100 to a BMI (Brain Machine Interface) is expected.

In addition, the biomedical electrode 100 can be used as a dry sensor that is simple and can be repeatedly used instead of a wet sensor that requires application of gel to a measurement portion. In addition, the biomedical electrode 100 can have flexibility that can reduce pain or discomfort to a subject (user) as compared to a dry sensor of a metal pin type with a spring. In addition, the biomedical electrode 100 can be mounted on a wearable device due to a reduction in size.

A biomedical sensor according to the embodiment will be described.

Figure 2:
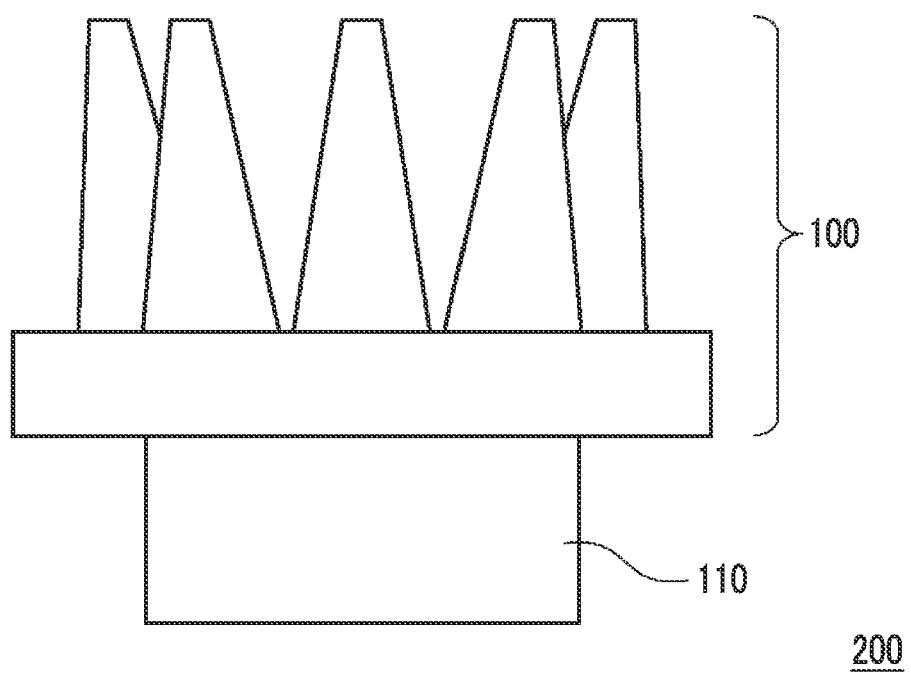
FIG. 2 is a schematic diagram showing a biomedical sensor according to the embodiment.

FIG. 2 is a schematic diagram showing the summary of a biomedical sensor 200.

The biomedical sensor 200 according to the embodiment includes the biomedical electrode 100 and may further include an external connection portion 110 connected to the biomedical electrode 100.

The external connection portion 110 may be detachably attached to the plate-shaped support portion 10 of the biomedical electrode 100 or may be fixed to the plate-shaped support portion 10.

From the viewpoint of durability, the external connection portion 110 includes at least an external electrode portion that is more rigid than the silicone rubber and has conductivity. The external electrode portion is formed of, for example, a metal. The external electrode portion can transmit a bioelectric signal detected by the biomedical electrode 100 to an external electronic component. The shape of the external electrode portion is not particularly limited and is configured to be a shape to which a connector or a wiring connectable to an electronic component can be attached. For example, the external connection portion 110 is configured with a metal snap button and has a structure that is electrically connected to an external wiring or an electrode of a substrate through a contact pin.

The biomedical sensor 200 may further include an electronic component that can be electrically connected through the external connection portion 110. As the electronic component, well-known components can be used depending on various uses. Examples of the electronic component include an amplifier, an AD converter, a CPU, a memory, a communication circuit, a wireless communication unit, an analog filter, a capacitor, a resistor, and a battery. Among the examples, one or more components may be modularized on a circuit board. As a result, the biomedical sensor 200 can be used as a wearable device.

In addition, the biomedical sensor 200 may be used in combination with another sensor such as an acceleration sensor, a temperature sensor, or a pressure sensor as the electronic component.

The biomedical sensor 200 includes one or more biomedical electrodes 100. The biomedical sensor 200 may be provided in an attachment jig to a living body such as a headgear or an arm band.

A biomedical signal measurement system according to the embodiment will be described.

The biomedical signal measurement system according to the embodiment includes the biomedical sensor 200. The biomedical signal measurement system may be a system (measurement device) that displays, analyzes, or stores data received from the biomedical sensor 200.

Hereinabove, the embodiment of the present invention has been described. However, the embodiment is an example of the present invention, and various configurations other than the above-described configuration can be adopted. In addition, the present invention is not limited to the above-described embodiment, and includes modifications, improvements, and the like within a range where the object of the present invention can be achieved.

EXAMPLES

Hereinafter, examples of the present invention will be described in detail. However, the present invention is not limited to the description of the examples.

Raw material components shown in Table 1 are as described below.
(Vinyl Group-Containing Organopolysiloxane (A))

(A1-1): first vinyl group-containing linear organopolysiloxane:vinyl group content=0.04 mol %, $Mn=2.2 \times 10^5$, $Mw=4.8 \times 10^5$), a vinyl group-containing dimethylpolysiloxane (the structure represented by Formula (1-1)) synthesized according to the following synthesis scheme 1

(A1-2): second vinyl group-containing linear organopolysiloxane:vinyl group content=0.92 mol %, a vinyl group-containing dimethylpolysiloxane (the structure represented by Formula (1-1) where $R^1$ and $R^2$ represent a vinyl group) synthesized according to the following synthesis scheme 2
(Organohydrogen Polysiloxane (B))

(B): organohydrogenpolysiloxane: manufactured by Momentive Inc. "TC-25D"
(Silica Particles (C))

(C): Silica fine particles (particle size: 7 nm, specific surface area: 300 $m^2$/g), manufactured by Nippon Aerosil Co., Ltd., "AEROSIL 300"
(Silane Coupling Agent (D))

(D-1): Hexamethyldisilazane (HMDZ), manufactured by Gelest Inc. "HEXAMETHYLDISILAZAE" (SIH6110.1)"

(D-2): divinyltetramethyldisilazane, manufactured by Gelest Inc., "1,3-DIVINYLTETRAMETHYLDISILAZANE (SID4612.0)"
(Platinum or Platinum Compound (E))

(E): platinum or a platinum compound: manufactured by Momentive Inc., "TC-25A"
(Water (F))

(F): pure water
(Metal Powder (G))

(G1): silver powder, manufactured by Tokuriki Honten Co., Ltd, trade name "TC-101", median size $d_{50}$: 8.0 μm, aspect ratio: 16.4, average long diameter: 4.6 μm
(Synthesis of Vinyl Group-Containing Organopolysiloxane (A))
[Synthesis Scheme 1: Synthesis of First Vinyl Group-Containing Linear Organopolysiloxane (A1-1)]

The first vinyl group-containing linear organopolysiloxane (A1-1) was synthesized according to the following Formula (5).

That is, 74.7 g (252 mmol) of octamethylcyclotetrasiloxane and 0.1 g of potassium siliconate were added to 300 mL separable flask including a cooling tube and a mixing impeller where the atmosphere was replaced with Ar gas. The solution was heated and stirred at 120° C. for 30 minutes. At this time, an increase in viscosity was observed.

Next, the solution was heated up to 155° C. and was continuously stirred for 3 hours. After 3 hours, 0.1 g (0.6 mmol) of 1,3-divinyltetramethyldisiloxane was added and was further stirred at 155° c. for 4 hours.

Further, after 4 hours, the solution was diluted with 250 mL of toluene, and was cleaned with water 3 times. After cleaning, the organic layer was cleaned with 1.5 L of methanol and was purified by precipitation to separate an oligomer and a polymer. The obtained polymer was dried at 60° C. under reduced pressure overnight. As a result, the first vinyl group-containing linear organopolysiloxane (A1-1) was obtained ($Mn=2.2 \times 10^5$, $Mw=4.8 \times 10^5$). In addition, the vinyl group content calculated by H-NMR spectrum measurement was 0.04 mol %.

Formula (5)

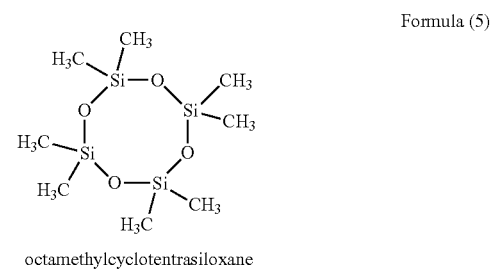

octamethylcyclotentrasiloxane

↓ potassium siliconate

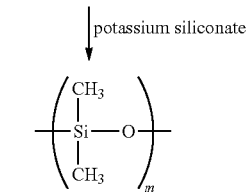

↓

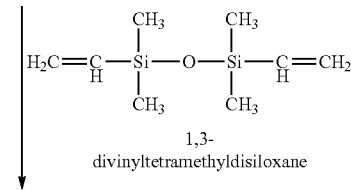

1,3-divinyltetramethyldisiloxane

↓

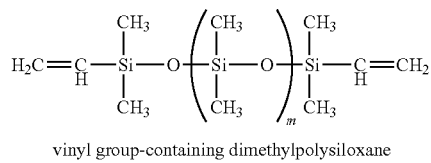

vinyl group-containing dimethylpolysiloxane

[Synthesis Scheme 2: Synthesis of Second Vinyl Group-Containing Linear Organopolysiloxane (A1-2)]

The second vinyl group-containing linear organopolysiloxane (A1-2) was synthesized as shown in the following Formula (6) using the same method as the synthesis step of (A1-1), except that 74.7 g (252 mmol) of octamethylcyclotetrasiloxane and 0.86 g (2.5 mmol) of 2,4,6,8-tetraethenyl-2,4,6,8-tetravinylcyclotetrasiloxane were used in the synthesis step of (A1-1). In addition, the vinyl group content calculated by H-NMR spectrum measurement was 0.92 mol %.

Formula (6)

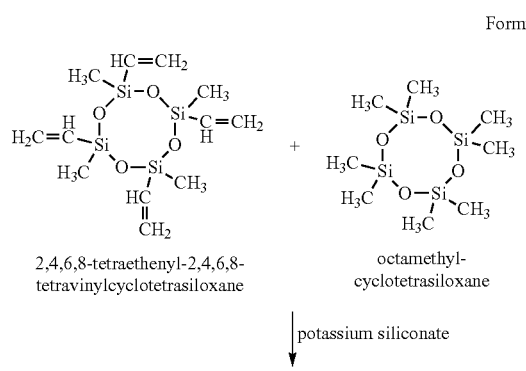

2,4,6,8-tetraethenyl-2,4,6,8-tetravinylcyclotetrasiloxane octamethylcyclotetrasiloxane

| potassium siliconate

-continued

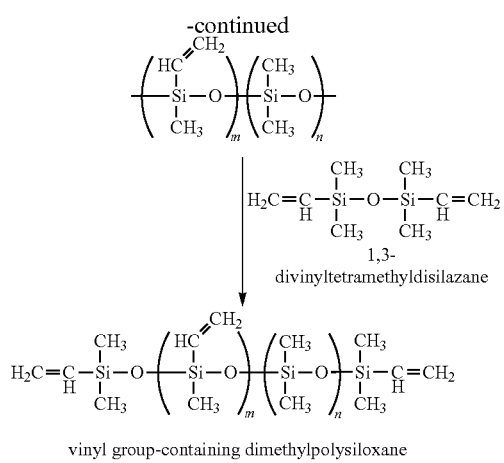

1,3-divinyltetramethyldisilazane vinyl group-containing dimethylpolysiloxane

<Preparation of Silicone Rubber-Based Curable Composition>

The silicone rubber-based curable composition was prepared as follows.

First, a mixture including 90% of the vinyl group-containing organopolysiloxane (A), the silane coupling agent (D), and the water (F) at a ratio shown in Table 1 below was kneaded in advance. Next, the silica particles (C) were further added to the mixture and kneaded. As a result, a kneaded material (silicone rubber compound) was obtained.

Here, the kneading after the addition of the silica particles (C) was performed through a first step of kneading the components under conditions of 60° C. to 90° C. in a nitrogen atmosphere for the coupling reaction and a second step of kneading the components under conditions of 160° C. to 180° C. for 2 hours in a reduced pressure atmosphere for removing the by-product (ammonia). Next, the kneaded material was cooled, the remaining 10% of the vinyl group-containing organopolysiloxane (A) was dividedly added twice, and the components were kneaded for 20 minutes.

Next, the organohydrogen polysiloxane (B) and the platinum or platinum compound (E) were added to 100 parts by weight of the obtained kneaded material (silicone rubber compound) at a ratio shown in Table 1 below, and the components were kneaded with a roll. As a result, the silicone rubber-based curable composition A (elastomer composition) was obtained.

TABLE 1

| | | | | Unit | A | B | C | D | E | F | G |
|---|---|---|---|---|---|---|---|---|---|---|---|
| Silicone Rubber-Based Curable Composition | Silicone Rubber Compound (Mixture) | Vinyl Croup-Containing Organopolysiloxane (A) | (A1-1) (A1-2) | Part(s) by Mass | 80 20 | 80 20 | 80 20 | 80 20 | 80 20 | 80 20 | 80 20 |
| | | Silica Particles (C) | | | 20 | 25 | 25 | 25 | 35 | 50 | 50 |
| | | Silane Coupling Agent (D) | (D-1) (D-2) | | 8.0 0.4 | 10.0 0.5 | 10.0 0.5 | 10.0 0.5 | 9.8 0.7 | 9.5 1.0 | 9.5 1.0 |
| | | Water (F) | | | 4.20 | 5.25 | 5.25 | 5.25 | 5.25 | 5.25 | 5.25 |
| | Catalyst | Platinum or Platinum Compound (E) | | Part(s) by Mass (with respect to 100 Part by Mass of Mixture) | 0.5 | 0.5 | 0.5 | 0.5 | 0.5 | 0.5 | 0.5 |
| | Crosslinking Agent | Organohydrogen Polysiloxane (B) | | | 1.36 | 1.81 | 2.69 | 3.77 | 4.53 | 2.26 | 4.53 |

<Preparation of Conductive Solution for Dip Coating>

13.7 parts by weight of the obtained silicone rubber-based curable composition A was immersed in 31.8 parts by weight of decane (solvent), the solution was stirred using a rotating and revolving mixer, 54.5 parts by weight of metal powder (G1) was added, and the components were kneaded with three rolls. As a result, a conductive paste (conductive solution for dip coating) was obtained.

<Preparation of Biomedical Electrode>

Example 1

The silicone rubber-based curable composition C was heated and cured at 180° C. and 10 MPa for 10 minutes using a mold including a molding space for the plate-shaped support portion and six pillar portions. As a result, a compact where the plate-shaped support portion and the six pillar portions were integrated was obtained.

Next, the distal end portions of all the pillar portions were obliquely cut to form an inclined surface in the distal end portion.

Using a sewing needle, a conductive wire A (manufactured by Mitsufuji Corporation, AGposs, thickness: 100d/

34f, tensile elongation at break: 29.3%) was made to pass the inside of each of the pillar portions of the obtained compact.

Next, only the distal end portion of the pillar portion (when the overall length of the pillar portion was represented by L, a region of about ½ L from the distal end) was dipped in <Conductive Solution for Dip Coating> and was heated and dried at 120° C. for 30 minutes. Next, post-curing was performed at 140° C. for 2 hours.

As a result, a biomedical electrode C shown in FIG. 4A was obtained. The distal end angle (the inclination angle θ of the inclined surface) shown in FIG. 4B was 32 degrees.

Examples 2 to 4

Biomedical electrodes D, E, and F were obtained using the same method as that of Example 1, except that a compact was obtained using each of the silicone rubber-based curable compositions D, E, and F instead of the silicone rubber-based curable composition C.

Comparative Examples 1 to 3

Biomedical electrodes A, B, and G were obtained using the same method as that of Example 1, except that a compact was obtained using each of the silicone rubber-based curable compositions A, B, and G instead of the silicone rubber-based curable composition C.

The obtained biomedical electrodes A to F were evaluated for the following evaluation items. The evaluation results are shown in Table 2.

Next, the top of the head of a subject was cleaned with alcohol and was well dried with a gauze.

Next, the system was set to a contact resistance measurement mode using control software.

Next, the distal end portion of the biomedical electrode 100 was brought into contact with the top of the head (measurement point: Cz) of the subject using a headgear, and when biomedical electrode 100 was pressed against the head of the subject, a pressing value (Ω) was measured as the contact resistance using the contact resistance measurement device.

The contact resistance of the biomedical electrode was evaluated based on the following evaluation criteria. The results are shown in Table 2.

A case where the contact resistance was lower than 40 kΩ was evaluated as A, a case where the contact resistance was 40 kΩ or higher and lower than 80 kΩ was evaluated as B, and a case where the contact resistance was 80 kΩ or higher was evaluated as C.

(Measurement Stability: Brain Wave Acquisition Success Ratio)
<Preparation of Electroencephalographic System>

As shown in FIG. 2, the external connection portion 110 (a metal snap button having a structure where an end portion of a cable is mountable) was mounted on the second surface 14 of the biomedical electrode 100 obtained in <Preparation of Biomedical Electrode> described above. A (1ch) preamplifier cable (manufactured by Unique Medical Co., Ltd., trade name: TF217-026), a biomedical amplifier (manufac-

TABLE 2

| | Unit | Comparative Example 1 | Comparative Example 2 | Example 1 | Example 2 | Example 3 | Example 4 | Comparative Example 3 |
|---|---|---|---|---|---|---|---|---|
| Biomedical Electrode | | A | B | C | D | E | F | G |
| Rubber Hardness A | | 20 | 30 | 36 | 40 | 50 | 60 | 70 |
| Contact Resistance | Ω | 90 | 83 | 34 | 66 | 53 | 47 | 82 |
| | | C | C | A | B | B | B | C |
| Brain Wave Acquisition Success Ratio | % | 50 | 70 | 90 | 90 | 100 | 100 | 100 |
| | | D | C | B | B | A | A | A |
| Discomfort during Wearing | | 1.0 | 1.2 | 1.8 | 1.8 | 2.5 | 2.5 | 3.3 |
| | | A | A | B | B | C | C | D |

<Rubber Hardness A>

Each of the obtained silicone rubber-based curable compositions A to G was pressed at 180° C. and 10 MPa for 10 minutes and was molded into a sheet shape having a thickness of 1 mm and was primarily cured. Next, the composition was secondarily cured at 180° C. for 2 hours to obtain a sheet-shaped silicone rubber (sheet). Six sheets having a thickness of 1 mm were laminated to prepare a specimen having a thickness of 6 mm. Using the obtained specimen, a type A durometer hardness (rubber hardness A) was measured at 37° C. according to JIS K 6253 (1997).

The rubber hardness A of each of the two samples was measured 10 times under conditions where n=5, and the average value thereof was obtained as a measured value. The results are shown in Table 2.
<Contact Resistance>

A second surface 14 (FIG. 4B) of the biomedical electrode 100 obtained in <Preparation of Biomedical Electrode> was attached to a contact resistance measurement device (Polymate Mini AP108, a wireless biosignal amplifier system, manufactured by Miyuki Giken Co., Ltd.).

tured by Unique Medical Co., Ltd., trade name: a potable biomedical amplifier EBA-100), and an oscilloscope were electrically connected to the external connection portion 110 in this order to prepare an electroencephalographic system.

Next, a headgear (a headgear that has a node arrangement according to the ten-twenty electrode system of the International Federation that was molded using a 3D printer) for electroencephalography was worn in the head of a subject.

Next, the top of the head of the subject was brought into contact with the distal end portion of the biomedical electrode 100 to determine whether or not a brain wave was able to be obtained based on a waveform displayed on a monitor of the oscilloscope (electroencephalography procedure).

This electroencephalography procedure was repeatedly performed on the same subject ten times (measurement times), and the number of times (the number of times of brain wave acquisition) a brain wave was able to be measured was recorded. A ratio (%) of the number of times of brain wave acquisition to the measurement times was set as "brain wave acquisition success ratio". The results are shown in Table 2.

When a brain wave was able to be measured, the baseline was constant, and the waveform was stable.

The measurement stability of the biomedical electrode was evaluated based on the following evaluation criteria. The results are shown in Table 2.

A case where the brain wave acquisition success ratio was higher than 90% and 100% or lower was evaluated as "A", a case where the brain wave acquisition success ratio was higher than 70% and 90% or lower was evaluated as "B", a case where the brain wave acquisition success ratio was higher than 50% and 70% or lower was evaluated as "C", and a case where the brain wave acquisition success ratio was 0% or higher and 50% or lower was evaluated as "D".

<Wearing Stability: Discomfort During Wearing>

While pressing the distal ends 22 of the six pillar portion 20 of the obtained biomedical electrode 100 against the back of the head of a subject, a probe of a push-pull gauge (manufactured by Nidec-Shimpo Corporation, trade name: Digital Force Gauge FGJN-2) was pressed against the second surface 14 of the biomedical electrode 100 at a constant load of 10 N. 1 minute after pressing, the subject evaluated wearability indices (1 to 4) based on the following sensory test evaluation criteria. This evaluation was performed for five subjects (one male in his twenties one female in her twenties, and one males in his thirties), and the average value of the wearability index was calculated. The results are shown in Table 2.

(Sensory Test Evaluation Criteria)
1: the subject felt the sense of contact but did not feel uneasy
2: the subject did not have pain but felt discomfort
3: the subject had pain but was able to endure pain only for a short period of time
4: the subject had pain but was not able to endure pain even for a short period of time The wearing stability of the biomedical electrode was evaluated based on the following evaluation criteria. The results are shown in Table 2.

A case where the wearability index was 1.0 or higher and 1.5 or lower was evaluated as "A", a case where the wearability index was higher than 1.5 and 2.0 or lower was evaluated as "B", a case where the wearability index was higher than 2.0 and 2.5 or lower was evaluated as "C", and a case where the wearability index was higher than 2.5 and 4.0 or lower was evaluated as "D".

It was found that, in the biomedical electrodes according to Examples 1 to 4, the contact resistance was lower than those of Comparative Examples 1, 2, and 4, the measurement stability was higher than those of Comparative Examples 1 and 2 and the wearing stability was higher than that of Comparative Example 4.

The present application claims priority based on Japanese Patent Application No. 2019-117492 filed on Jun. 25, 2019, the entire contents of which are incorporated herein by reference.

REFERENCE SIGNS LIST

10: plate-shaped support portion
12: first surface
14: second surface
20: pillar portion
22: distal end
24: base end
26: distal end portion
28: inclined surface
30: conductive resin layer
50: center portion
60: conductive wire
100: biomedical electrode
110: external connection portion
200: biomedical sensor

What is claim is:

1. A biomedical electrode comprising:
a plate-shaped support portion;
an elastic pillar portion that is provided on a first surface of the plate-shaped support portion; and
a conductive resin layer that is formed to cover a distal end of the elastic pillar portion, wherein when measured at 37° C. according to JIS K 6253 (1997), a type A durometer hardness of a surface of the elastic pillar portion is higher than 35 and equal to or lower than 65.

2. The biomedical electrode according to claim 1, further comprising:
a conductive wire that is electrically connected to the conductive resin layer and is arranged in the elastic pillar portion from a distal end side of the elastic pillar portion toward a base end side of the elastic pillar portion.

3. The biomedical electrode according to claim 1, wherein a plate-shaped support member and an elastic pillar portion are formed of an integrated member.

4. The biomedical electrode according to claim 1, wherein the elastic pillar portion is formed of an insulating elastic member including a silicone rubber.

5. The biomedical electrode according to claim 1, wherein the conductive resin layer includes a conductive filler and a silicone rubber.

6. The biomedical electrode according to claim 5, wherein a content of the conductive filler is 30 mass % or higher and 90 mass % or lower with respect to 100 mass % of the silicone rubber.

7. The biomedical electrode according to claim 5, wherein the conductive filler includes one or more selected from the group consisting of metal particles, metal fiber, metal-coated fiber, carbon black, acetylene black, graphite, carbon fiber, carbon nanotube, a conductive polymer, conductive polymer-coated fiber, and metal nanowire.

8. The biomedical electrode according to claim 1, wherein a thickness of the conductive resin layer is 5 µm or more and 200 µm or less.

9. The biomedical electrode according to claim 1, wherein the elastic pillar portion is formed in a truncated conical shape.

10. The biomedical electrode according to claim 1, wherein a plurality of the elastic pillar portions are provided, and
the plurality of elastic pillar portions are arranged to surround a center portion of the plate-shaped support portion.

11. The biomedical electrode according to claim 1, wherein the biomedical electrode is used as an electroencephalographic electrode.

12. A biomedical sensor comprising the biomedical electrode according to claim 1.

13. A biomedical signal measurement system comprising the biomedical sensor according to claim 12.

* * * * *